United States Patent [19]

Machin

[11] Patent Number: 4,649,160
[45] Date of Patent: Mar. 10, 1987

[54] SUBSTITUTED PHENOXY-AMINOPROPANOLS

[75] Inventor: Peter J. Machin, London, United Kingdom

[73] Assignee: Hoffmann-La Roche Inc., Nutley, N.J.

[21] Appl. No.: 773,390

[22] Filed: Sep. 6, 1985

Related U.S. Application Data

[63] Continuation of Ser. No. 505,504, Jun. 17, 1983, abandoned, which is a continuation of Ser. No. 267,497, May 28, 1981, abandoned.

[30] Foreign Application Priority Data

May 2, 1980 [GB] United Kingdom ............... 8017583
Mar. 17, 1981 [GB] United Kingdom ............... 8108345

[51] Int. Cl.$^4$ .......................................... A61K 31/135
[52] U.S. Cl. .................................. 514/652; 514/651;
549/555; 549/559; 549/560; 564/349; 568/331;
568/609; 568/610
[58] Field of Search .............. 564/347, 349; 514/651, 514/652

[56] References Cited

U.S. PATENT DOCUMENTS 3,674,840 7/1972 Grandstrom et al. .......... 564/347 X
3,723,476 3/1973 Nakanishi et al. ............ 564/349 X
3,996,382 12/1976 Berntsson et al. ............ 564/349 X
4,252,984 2/1981 Manoury et al. ................... 564/349

FOREIGN PATENT DOCUMENTS 2020864 11/1970 Fed. Rep. of Germany ...... 564/349
2316727  4/1972 Fed. Rep. of Germany ...... 564/349
2400693 10/1973 Fed. Rep. of Germany ...... 564/349
1320453  6/1973 United Kingdom ................ 564/349
2079750  1/1982 United Kingdom ................ 564/349

Primary Examiner—Robert V. Hines
Attorney, Agent, or Firm—Jon S. Saxe; Bernard S. Leon; Matthew Boxer

[57] ABSTRACT

Substituted phenoxy-aminopropanols of the formula

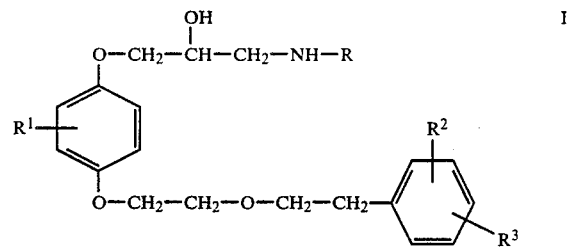

wherein R is a branched-chain alkyl of 3 or 4 carbon atoms, $R^1$ is hydrogen, halogen or lower alkyl and $R^2$ and $R^3$, independently, are hydrogen, halogen, lower alkyl, lower alkoxy or lower alkylthio, and pharmaceutically acceptable acid addition salts thereof, are described. A process for their preparation, as well as pharmaceutical preparations containing them are also described. The compounds of formula I and their salts possess cardioselective β-adrenergic blocking activity and antihypertensive activity.

15 Claims, No Drawings

SUBSTITUTED PHENOXY-AMINOPROPANOLS

This is a continuation of application Ser. No. 505,504 filed June 17, 1983 which is a continuation of parent U.S. Ser. No. 267,497, filed May 28, 1981, both now abandoned.

BRIEF DESCRIPTION OF THE INVENTION

The invention relates to compounds of the formula

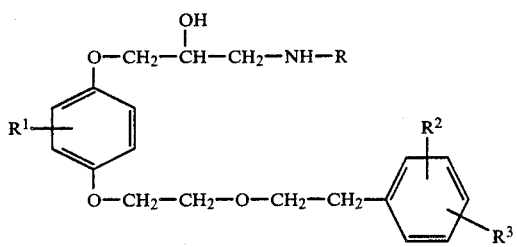

I wherein R is a branched-chain alkyl group containing 3 or 4 carbon atoms, $R^1$ is hydrogen, halogen, or lower alkyl, and $R^2$ and $R^3$ each, independently, are hydrogen, halogen, lower alkyl, lower alkoxy or lower alkylthio, or a pharmaceutically acceptable acid addition salt thereof. The compounds of formula I and their pharmaceutically acceptable acid addition salts possess cardioselective β-adrenergic blocking activity and antihypertensive activity.

In another aspect, the invention relates to intermediates of the formulas

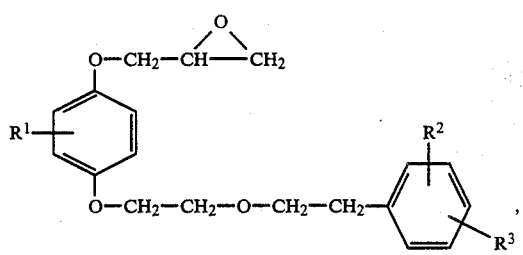

II

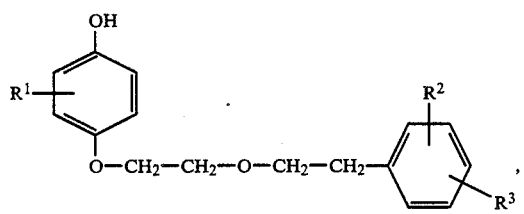

VI

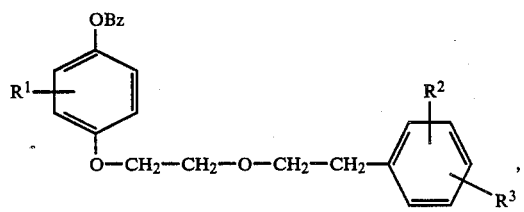

VIII

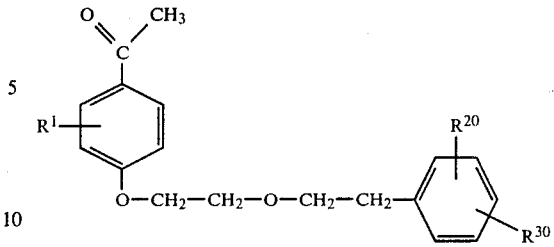

X wherein $B_z$ is benzyl, $R^{20}$ and $R^{30}$ each, independently, are hydrogen, halogen, lower alkyl, or lower alkoxy, and $R^1$, $R^2$ and $R^3$ are as previously described.

In yet another aspect, the invention relates to a process for the preparation of the compounds of formula I and to pharmaceutical preparations containing the compounds of formula I.

DETAILED DESCRIPTION OF THE INVENTION

The substituted phenoxy-aminopropanols of the invention are compounds of the formula

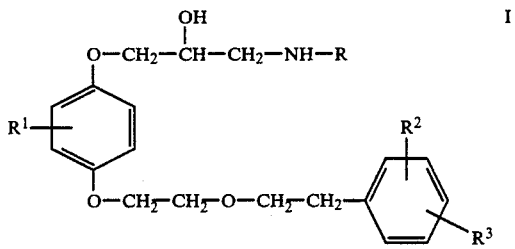

I wherein R is a branched-chain alkyl containing 3 to 4 carbon atoms, $R^1$ is hydrogen, halogen, or lower alkyl, and $R^2$ and $R^3$ each, independently, are hydrogen, halogen, lower alkyl, lower alkoxy, or lower alkylthio, or a pharmaceutically acceptable acid addition salt thereof.

As used herein, the term "lower alkyl" denotes a straight-chain or branched-chain alkyl group which contains from 1 to 4 carbon atoms, for example, methyl, ethyl, propyl, isopropyl, butyl, isobutyl, tert.butyl and the like. The "branched-chain alkyl group containing 3 or 4 carbon atoms" denoted by R is isopropyl, isobutyl, sec.butyl or tert.butyl. The term "lower alkoxy" denotes a straight-chain or branched-chain alkoxy group which contains from 1 to 4 carbon atoms, for example, methoxy, ethoxy, propoxy, isopropoxy, butoxy and the like. The term "lower alkylthio" denotes an alkylthio group which contains from 1 to 4 carbon atoms, for example, methylthio, ethylthio and the like. The term "halogen" denotes fluorine, chlorine, bromine and iodine.

A preferred group of compounds of formula I comprises those wherein $R^1$ is present in the ortho-position to the 3-alkylamino-2-hydroxypropoxy group, $R^3$ is hydrogen and R and $R^2$ are as previously described.

A more preferred group of compounds of formula I comprises those in which R is isopropyl or tert.butyl group.

Particularly preferred compounds of formula I are:
1-[4-[2-(4-methylphenethyloxy)ethoxy]phenoxy]-3-isopropylamino-2-propanol,
1-[4-[2-(4-methylthiophenethyloxy)ethoxy]phenoxy]-3-isopropylamino-2-propanol, 1-[tert.butylamino-3-[4-(4-phenethyloxyethoxy)phenoxy]-2-propanol,
1-[2-chloro-4-[2-(phenethyloxy)ethoxy]phenoxy]-3-isopropylamino-2-propanol,
1-[2-methyl-4-[2-(phenethyloxy)ethoxy]phenoxy]-3-isopropylamino-2-propanol,
1-[4-[2-(4-methoxyphenethyloxy)ethoxy]phenoxy]-3-isopropylamino-2-propanol,
1-[4-[2-(4-chlorophenethyloxy)ethoxy]phenoxy]-3-isopropylamino-2-propanol,
1-[2-fluoro-4-[2-(4-fluorophenethyloxy)ethoxy]phenoxy]-3-isopropylamino-2-propanol
1-[3-fluoro-4-[2-(4-fluorophenethyloxy)ethoxy]phenoxy]-3-isopropylamino-2-propanol and
1-[4-[2-(2,4-difluorophenethyloxy)ethoxy]phenoxy]-3-isopropylamino-2-propanol.

Especially preferred compounds of formula I are:
1-Isopropylamino-3-[4-(2-phenethyloxyethoxy)phenoxy]-2-propanol and
1-[4-[2-(4-fluorophenethyloxy)ethoxy]phenoxy]-3-isopropylamino-2-propanol.

According to the process of the invention, the substituted phenoxyaminopropanol derivatives of formula I and their pharmaceutically acceptable acid addition salts are prepared by (a) reacting an epoxide of the formula

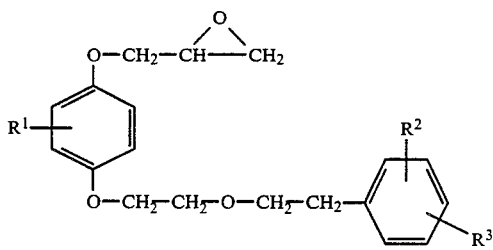

wherein $R^1$, $R^2$ and $R^3$ are as previously described, with an amine of the formula

$$H_2N-R \qquad III$$

wherein R are as previously described, or (b) reacting an alkali metal derivative of a phenol of the formula

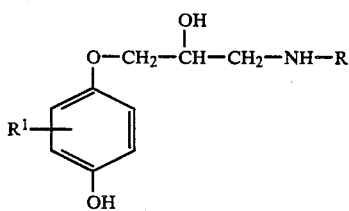

wherein R and $R^1$ are as previously described, with a compound of the formula

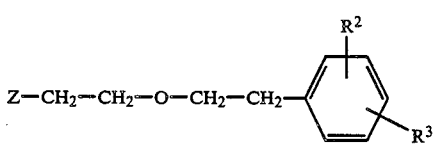

wherein $R^2$ and $R^3$ are as previously described and Z is lower alkylsulfonyloxy or arylsulfonyloxy, and (c) if desired, resolving a racemate of formula I into the optical isomers, and/or (d) if desired, converting a compound of formula I into a pharmaceutically acceptable acid addition salt.

The reaction of an epoxide of formula II with an amine of formula III, which are known compounds, in accordance with process embodiment (a) is carried out in a known manner. The treatment can be carried out in the presence or absence of an inert organic solvent. When an inert organic solvent is used, this can be, for example, a lower alkanol such as methanol, ethanol or the like. Alternatively, an excess of an amine of formula III can be used and can thereby serve as the solvent. The treatment is advantageously carried out at a temperature in the range of from about 0° C. to about room temperature, preferably at room temperature, and under atmospheric pressure.

The reaction of an alkali metal derivative of a phenol of formula IV with a compound of formula V in accordance with process embodiment (b) is conveniently carried out in an inert organic solvent. Examples of inert organic solvents which can be used are dimethylformamide, dioxane, dimethoxyethane and tetrahydrofuran, with dimethylformamide being preferred. The alkali metal derivative of a phenol of formula IV is preferably formed in situ from a corresponding phenol and an alkali metal, an alkali metal hydride or an alkali metal amide, preferably an alkali metal hydride and preferably sodium hydride. The reaction is advantageously carried out at an elevated temperature, preferably at about 60° C. The group Z in the compounds of formula V is preferably a lower alkylsulfonyloxy group, for example, methanesulfonyloxy, but it can also be an arylsulfonyloxy group, for example, benzenesulfonyloxy or p-toluenesulfonyloxy.

It will be appreciated that the compounds of formula I hereinbefore contain an asymmetric carbon atom and can occur in racemic or optically active form. The invention includes within its scope the racemates as well as the optically active forms. If desired, a racemate can be resolved into the optical isomers in accordance with process embodiment (c) using known methods, for example, by fractional crystallization of salts formed with optically active acids. It will also be appreciated that the phenol starting material of formula IV can be used in optically active form to give a corresponding optically active form of the desired compound of formula I.

The compounds of formula I can be converted into pharmaceutically acceptable acid addition salts in accordance with process embodiment (d) by treatment with pharmaceutically acceptable inorganic acids, for example, hydrochloric acid, hydrobromic acid, sulfuric acid, phosphoric acid and the like and with pharamaceutically acceptable organic acids, for example, acetic acid, tartaric acid, citric acid, fumaric acid, maleic acid, malic acid, methanesulfonic acid, p-toluenesulfonic acid and the like.

The epoxides of formula II used as starting materials in process embodiment (a) also form part of the invention. They can be prepared by reacting an alkali metal derivative of a phenol of the formula

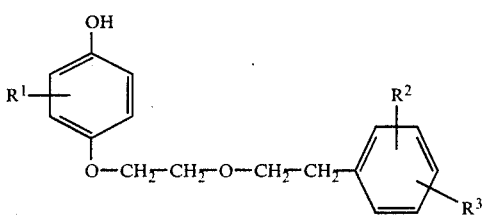 VI

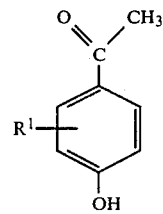 IX wherein $R^1$, $R^2$ and $R^3$ are as previously described, with epichlorohydrin or epibromohydrin.

The reaction of an alkali metal derivative of a phenol of formula VI with epichlorohydrin or epibromohydrin, preferably epichlorohydrin, can be carried out in a manner analogous to that described earlier in connection with the reaction of an alkali metal derivative of a phenol of formula IV with a compound of formula V.

The phenols of formula VI hereinbefore are also form part of the invention. They can be prepared by reacting an alkali metal derivative of a phenol of the formula

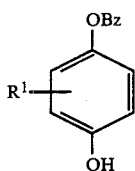 VII wherein $R^1$ is as previously described and Bz is benzyl, with a compound of formula V hereinbefore and debenzylating the resulting compound of the formula

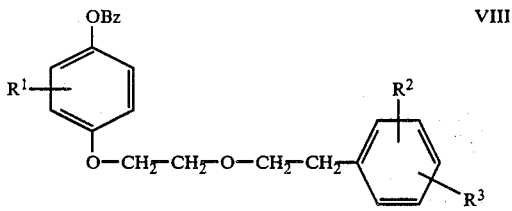 VIII wherein $R^1$, $R^2$, $R^3$ and Bz are as previously described.

The reaction of an alkali metal derivative of a phenol of formula VII with a compound of formula V can be carried out in a manner analogous to that described earlier in connection with the reaction of an alakli metal derivative of a phenol of formula IV with a compound of formula V.

The debenzylation of a compound of formula VIII can be carried out in a known manner; for example, using hydrogen in the presence of a catalyst, for example, palladium/carbon and the like, or using hydrogen bromide in glacial acetic acid.

The phenols of formula VII, insofar as they are not known, can be prepared as described in the Examples hereinafter or in analogy thereto.

The compounds of formula VIII are also part of the invention.

Another method for the preparation of phenols of formula VI in which $R^2$ and $R^3$ each is hydrogen, halogen, lower alkyl or lower alkoxy comprises reacting an alkali metal derivative of a phenol of the formula wherein $R^1$ are as previously described, with a compound of formula V hereinbefore in which $R^2$ and $R^3$ each is ahydrogen, halogen, lower alkyl or lower alkoxy group and replacing the acetyl group in the resulting compound of the formula

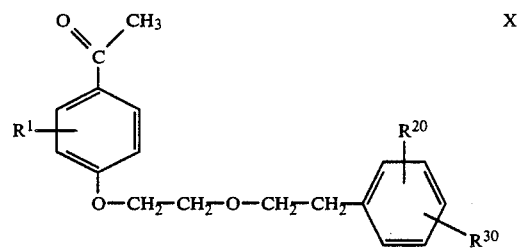 X wherein $R^1$ are as previously described and $R^{20}$ and $R^{30}$ each is hydrogen, halogen, lower alkyl or lower alkoxy, by a hydroxy group.

The reaction of an alkali metal derivative of a phenol of formula IX with a compound of formula V defined in the preceding paragraph can be carried out in a manner analogous to that described earlier in connection with the reaction of an alkali metal derivative of a phenol of formula IV with a compound of formula V.

The replacement of the acetyl group in a compound of formula X by a hydroxy group can be carried out in a known manner; for example, by oxidation with an organic peracid such as 3-chloroperbenzoic acid, conveniently in an inert organic solvent such as an aliphatic hydrocarbon, for example, methylene chloride, followed by treatment with an alkali metal lower alkoxide in the corresponding lower alkanol, for example, sodium ethoxide in ethanol.

The phenols of formula IX, insofar as they are not known, can be prepared as described in the Examples hereinafter or in analogy thereto.

The compounds of formula X also form part of the invention.

The phenol starting materials of formula IV hereinbefore are known compounds or analogues of known compounds which can be prepared in a customary manner.

The starting materials of formula V hereinbefore are known compounds or analogues of known compounds and can be prepared, for example, by firstly reacting an alcohol of the formula

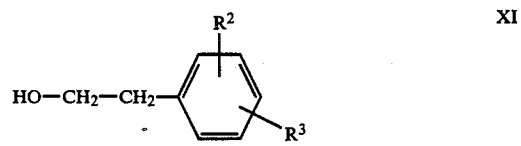 XI wherein $R^2$ and $R^3$ are as previously described, with chloroacetic acid to give an acid of the formula

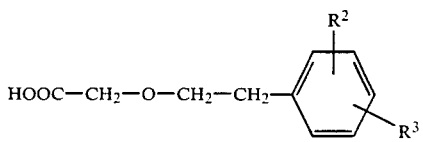

wherein $R^2$ and $R^3$ are as previously described.

The reaction of an alcohol of formula XI, which is a known compound or an analogue of a known compound obtainable in a customary manner, with chloroacetic acid can be carried out in the presence of an inert organic solvent such as dimethylformamide or dimethyl sulfoxide and in the presence of an alkali metal base such as an alkali metal hydride, for example, sodium hydride, at an elevated temperature, for example, at about 60°–120° C.

An acid of formula XII is subsequently reduced to give an alcohol of the formula

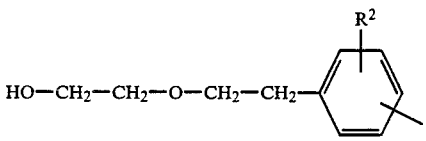

wherein $R^2$ and $R^3$ are as previously described.

The reduction of an acid of formula XIII is carried out in a known manner; for example, using lithium aluminum hydride in an inert organic solvent such as tetrahydrofuran at about room temperature.

Finally, an alcohol of formula XIII is converted into a compound of formula V by sulfonylation. This sulfonylation is carried out in a known manner; for example, by reaction with a lower alkylsulfonyl or arylsulfonyl halide, for example, methanesulfonyl chloride and the like, in the precense of a tertiary organic base such as triethylamine or pyridine at about room temperature.

The substituted phenoxy-aminopropanol derivatives provided by the present invention possess cardioselective $\beta$-adrenergic blocking activity and may accordingly be used for the prophylaxis and treatment of diseases of the heart such as, for example, angina pectoris and cardiac arrhythmias. They also possess antihypertensive activity and may thus be used as antihypertensive agents.

The cardioselective $\beta$-blocking activity of the present substituted phenoxyaminopropanol derivatives at $\beta_1$- and $\beta_2$-adrenoceptors can be demonstrated using standard test procedures. In one such test procedure, this activity is measured in rats by determining the dosage in μg/kg i.v. of substance being tested which is required to produce a 50% reduction in isoprenaline-induced tachycardia [this dosage being expressed as the $ED_{50}(HR)$] and a 50% reduction in isoprenaline-induced depressor responses [this dosage being expressed as the $ED_{50}(BP)$]. Where the $ED_{50}(BP)$ is significantly greater than the $ED_{50}(HR)$, the test substance is more selective in blocking $\beta_1$- than $\beta_2$-adrenoceptors, that is, cardioselective.

The results obtained in the foregoing test with representative substituted phenoxy-aminopropanol derivatives provided by this invention and atenolol, a well-known and widely used cardioselective $\beta$-adrenergic blocking agent, are given in the following Table:

TABLE

| Derivative | $ED_{50}$ (HR) (μg/kg i.v.) | $ED_{50}$ (BP) (μg/kg i.v.) |
|---|---|---|
| 1-Isopropylamino-3-[4-(2-phenethyloxyethoxy)phenoxy]-2-propanol hydrochloride | 15 | >2000 |
| 1-Tert.butylamino-3-[4-(2-phenethyloxyethoxy)phenoxy]-2-propanol hydrochloride | 18 | 979 |
| 1-[2-Chloro-4-[2-(phenethyloxy)ethoxy]phenoxy]-3-isopropylamino-2-propanol hydrochloride | 25 | 834 |
| 1-[4-[2-(4-Fluorophenethyloxy)ethoxy]phenoxy]-3-isopropylamino-2-propanol hydrochloride | 3 | >2000 |
| Atenolol | 91 | 2130 |

The substituted phenoxy-aminopropanol derivatives of formula I provided by the invention can be used as medicaments; for example, in the form of pharmaceutical preparations which contain them in association with a compatible pharmaceutical carrier material. This carrier material can be an inert organic or inorganic carrier material suitable for enteral, for example, oral and the like, or parenteral administration. Examples of such carrier materials are water, gelatin, talc, starch, magnesium stearate, gum arabic, vegetable oils, polyalkyleneglycols, petroleum jelly and the like. The pharmaceutical preparations can be produced in a conventional manner and finished dosage forms can be solid dosage forms, for example, tablets, dragees, suppositories, capsules and the like, or liquid dosage forms, for example, solutions, suspensions, emulsions and the like. The pharmaceutical preparations may be subjected to conventional pharmaceutical operations such as sterilization and/or may contain conventional adjuvants such as preservatives, stabilizers, wetting agents, buffers, salts for varying the osmotic pressure and like.

The substituted phenoxy-aminopropanol derivatives provided by the invention may be administered to adults in an amount of approximately 1 mg/kg to 10 mg/kg per day in a single dosage or in divided dosages. It will be appreciated that this dosage range is given by way of example and that it can be varied upwards or downwards depending on factors such as the particular substituted phenoxy-aminopropanol derivative being administered the route of administration and the requirements of the warm-blooded animal as determined by the practitioner.

The Examples which follow further illustrate the invention: All temperatures are in degrees Centigrade unless otherwise specified.

EXAMPLE 1

Preparation of 1-isopropylamino-3-[4-(2-phenethyloxyethoxy)phenoxy]-2-propanol hydrochloride 4.5 g of 1-isopropylamino-3-(4-hydroxyphenoxy)-2-propanol in 20 ml of dimethylformamide were treated with 0.96 g of a 50% sodium hydride dispersion in mineral oil and the mixture was stirred for 5 minutes. 4.88 g of 2-(2-phenylethoxy)ethyl methanesulfonate were added and the mixture was heated at 60° C. for 0.5 hour with stirring. The mixture was evaporated to dryness and the residue was partitioned between 2N sodium hydroxide solution and dichloromethane. The organic phase was separated, washed well with water, dried over sodium sulfate, filtered and evaporated. The residue was dissolved in 20 ml of ethanol, saturated with hydrogen chloride and the solution was evaporated to dryness. The crystalline residue was recrystallized from isopropanol to give 4.2 g (51%) of 1-isopropylamino-3-[4-(2-phenethyloxyethoxy)phenoxyl-2-propanol hydrochloride of melting point 105°–107° C.

The 2-(2-phenylethoxy)ethyl methanesulfonate used as the starting material can be prepared as follows:

(a) 6.1 g of phenethyl alcohol in 100 ml of dimethylformamide were treated with 4.8 g of a 50% sodium hydride dispersion in mineral oil and the mixture was stirred for 10 minutes at 60° C. 4.73 g of chloroacetic acid were added and the mixture was heated at 60° C. for 0.5 hour with stirring. The mixture was evaporated to dryness and the residue was partitioned between water and diethyl ether. The aqueous phase was acidified to pH 1 with concentrated hydrochloric acid and extracted with ethyl acetate. The organic phase was washed with water, dried over sodium sulfate, filtered and evaporated to dryness. The residue was recrystallized from ethyl acetate/hexane to give 7.65 g (85%) of 2-phenylethoxyacetic acid of melting point 46°–48° C.

(b) The 2-phenylethoxyacetic acid obtained according to the preceding paragraph was dissoled in 50 ml of tetrahydrofuran and the solution was added dropwise over a period of 10 minutes to a stirred suspension, cooled in an ice-bath, of 1.62 g of lithium aluminum hydride in 50 ml of tetrahydrofuran. The mixture was stirred at room temperature for 0.5 hour. The excess lithium aluminum hydride was destroyed by the addition of 1.6 ml of water, then 1.6 ml of 15% aqueous sodium hydroxide solution and finally 5 ml of water. The inorganic solids were removed by filtration, washed well with diethyl ether and the filtrates were evaporated to give 6.50 g (92%) of 2-(2-phenylethoxy)ethanol in the form of an oil which was homogenous according to chromatography. This product can be distilled under reduced pressure; boiling point 140°–142° C./15 mm Hg.

(c) The 2-(2-phenylethoxy)ethanol obtained according to the preceding paragraph was dissolved in 100 ml of pyridine. The solution was treated with 4.48 g of methanesulfonyl chloride and the mixture was stirred at room temperature for 0.5 hour. The solvent was removed by evaporation and the residue was partitioned between ethyl acetate and 2N hydrochloric acid. The organic phase was washed with water, dried over sodium sulfate, filtered and evaporated to give 8.1 g (85%) of 2-(2-phenylethoxy)ethyl methanesulfonate in the form of an oil which was homogeneous according to chromatography.

EXAMPLE 2

Preparation of 1-[4-[2-(4-fluorophenethyloxy)-ethoxy]-phenoxy]-3-isopropylamino-2-propanol hydrochloride In a manner analogous to that described in the first paragraph of Example 1, from 1.69 g of 1-isopropylamio-3-(4-hydroxyphenoxy)-2-propanol and 1.97 g of 2-[2(4-fluorophenyl)ethoxy]ethyl methanesulfonate there were obtained 1.6 g (50%) of 1-[4-[2-(4-fluorophenethyloxy)-ethoxy]phenoxy]-3-isopropylamino-2-propanol hydrochloride of melting point 88°–92° C. (from isopropanol).

The 2-[2-(4-fluorophenyl)ethoxy]ethyl methanesulfonate used as the starting material can be prepared as follows:

(a) 7.0 g of 4-fluorophenethyl alcohol were reacted with 4.73 g of chloroacetic acid in a manner analogous to that described in Example 1(a) to give 7.8 g (79%) of 2-(4-fluorophenyl)ethoxyacetic acid of melting point 82°–85° C. (from methylcyclohexane).

(b) The 2-(4-fluorophenyl)ethoxyacetic acid obtained according to the preceding paragraph was reduced with lithium aluminum hydride in a manner analogous to that described in Example 1(b) to give 6.6 g (91%) of 2-[2-(4-fluorophenyl)-ethoxy]ethanol in the form of an oil which was homogeneous according to chromatography.

(c) The 2-[2-(4-fluorophenyl)ethoxy]ethanol obtained according to the preceding paragraph was sulfonylated with methanesulfonyl chloride in a manner analogous to that described in Example 1(c) to give 8.2 g (87%) of 2-[2-(4-fluorophenyl)ethoxy]ethyl methanesulfonate in the form of an oil which was homogeneous according to chromatography.

EXAMPLE 3

Preparation of 1-[4-[2-(4-methylphenethyloxy)-ethoxy]-phenoxy]-3-iospropylamino-2-propanol hydrochloride In a manner analogous to that described in the first paragraph of Example 1, from 1.69 g of 1-isopropylamino-3-(4-hydroxyphenoxy)-2-propanol and 1.94 g of 2-[2(4-methylphenyl)ethoxy]ethyl methanesulfonate there were obtained 1.6 g (50%) of 1-[4-[2-(4-methylphenethyloxy)-ethoxy]phenoxy]-3-isopropylamino-2-propanol hydrochloride of melting point 104°–106° C. (from isopropanol).

The 2-[2-(4-methylphenyl)ethoxy]ethyl methanesulfonate used as the starting material can be prepared as follows:

(a) 6.8 g of 4-methylphenethyl alcohol were reacted with 4.73 g of chloroacetic acid in a manner analogous to that described in Example 1(a) to give 8.1 g (84%) of 2-(4-methylphenyl)ethoxyacetic acid of melting point 65°–67° C. (from methylcyclohexane).

(b) The 2-(4-methylphenyl)ethoxyacetic acid obtained according to the preceding paragraph was reduced with lithium aluminum hydride in a manner analogous to that described in Example 1(b) to give 6.6 g (88%) of 2-[2-(4-methylphenyl)ethoxy]ethanol in the form of an oil which was homogeneous according to chromatography.

(c) The 2-[2-(4-methylphenyl)ethoxy]ethanol obtained according to the preceding paragraph was sulfonylated with methanesulfonyl chloride in a manner analogous to that described in Example 1(c) to give 7.8 g (83%) of 2-[2-(4-methylphenyl)ethoxy]ethyl methanesulfonate in the form of an oil which was homogeneous according to chromatography.

EXAMPLE 4

Preparation of 1-[4-[2-(4-methylthiophenethyloxy)ethoxy]phenoxy]-3-isopropylamino-2-propanol hydrochloride In a manner analogous to that described in the first paragraph of Example 1, from 1.69 g of 1-isopropylamino-3-(4-hydroxyphenoxy)-2-propanol and 2.16 g of 2-[2-(4-methylthiophenyl)ethoxy]ethyl methanesulfonate there were obtained 1.40 g (41%) of 1-[4-[2-(4-methylthiophenethyloxy)ethoxy]phenoxy]-3-isopropylamino-2-propanol hydrochloride of melting point 98°–101° C. (from ethyl acetate).

The 2-[2-(4-methylthiophenyl)ethoxy]ethyl methanesulfonate used as the starting material can be prepared as follows:

(a) 6.27 g of 4-methylthiophenethyl alcohol in 100 ml of dimethyl sulfoxide were treated with 3.58 g of a 50% sodium hydride dispersion in mineral oil and the mixture was stirred at 60° C. for 10 minutes. 3.53 g of chloroacetic acid were added and the heating was continued at 80° C. for 3 hours while stirring. The mixture was cooled, poured into water and washed with ethyl acetate. The aqueous phase was acidified to pH 1 with concentrated hydrochloric acid and extracted with ethyl acetate. The organic phase was separated, washed well with water, dried over sodium sulfate, filtered and evaporated to dryness. The residue was recrystallized from toluene/hexane to give 3.89 g (46%) of 2-(4-methylthiophenyl)ethoxyacetic acid of melting point 58°–60° C.

(b) The 2-(4-methylthiophenyl)ethoxyacetic acid obtained according to the preceding paragraph was reduced with lithium aluminum hydride in a manner analogous to that described in Example 1(b) to give 1.97 g (54%) of 2-[2-(4-methylthiophenyl)ethoxy]ethanol in the form of an oil which was homogeneous according to chromatography.

(c) The 2-[2-(4-methylthiophenyl)ethoxy]ethanol obtained according to the preceding paragraph was sulfonylated with methanesulfonyl chloride in a manner analogous to that described in Example 1(c) to give 2.41 g (90%) of 2-[2-(4-methylthiophenyl)ethoxy]ethyl methanesulfonate in the form of an oil which was homogeneous according to chromatography.

EXAMPLE 5

Preparation of 1-tert.butylamino-3-[4-(2-phenethyloxyethoxy)phenoxy]-2-propanol hydrochloride In a manner analogous to that described in the first paragraph of Example 1, but using 1-tert.butylamino-3-(4-hydroxyphenoxy)-2-propanol in place of 1-isopropylamino-3-(4-hydroxyphenoxy)-2-propanol, there was obtained 1-tert.butylamino-3-[4-(2-phenethyloxyethoxy)phenoxy]-2-propanol hydrochloride of melting point 87°–88° C. (from ethanol/diethyl ether).

EXAMPLE 6

Preparation of 1-isopropylamino-3-[4-(2-phenethyloxyethoxy)phenoxy]-2-propanol hydrochloride 3.09 g of 4-(2-phenethyloxyethoxy)phenol were dissolved in 50 ml of dimethylformamide and the solution was stirred for 5 minutes with 0.58 g of a 50% sodium hydride dispersion in mineral oil. 10 ml of epichlorohydrin were added and the solution was stirred at 60° C. for 0.5 hour. The solvent and excess epichlorohydrin were removed by evaporation under reduced pressure and the residue was partitioned between ethyl acetate and water. The organic phase was separated, dried over sodium suflate, filtered and evaporated to give 3.2 g of epoxide which, without further purification, was dissolved in 50 ml of ethanol containing 15 ml of isopropylamine. The mixture was then left to stand at room temperature overnight. The solution was evaporated to dryness and the residue was converted into 2.7 g (59%) of 1-isopropylamino-3-[4-(2-phenethyloxyethoxy)phenoxy]-2-propanol hydrochloride. This salt was identical with the salt obtained according to the first paragraph of Example 1.

The 4-(2-phenethyloxyethoxy)phenol used as the starting material can be prepared as follows:

(a) 10 g of 4-benzyloxyphenol in 120 ml of dimethylformamide were treated with 2.4 g of a 50% sodium hydride dispersion in mineral oil and the mixture was stirred for 5 minutes. 12.2 g of 2-(2-phenylethoxy)ethyl methanesulfonate [prepared as described in Example 1(a)] were added and the mixture was heated at 60° C. for 0.5 hour with stirring. The mixture was evaporated to dryness and the residue was partitioned between 2N sodium hydroxide and ethyl acetate. The organic phase was separated, washed well with water, dried over sodium sulfate, filtered and evaporated. The residue was recrystallized from methylcyclohexane to give 16.1 g (93%) of 1-benzyloxy-4-(2-phenethyloxyethoxy)benzene of melting point 46°–49° C.

(b) The 1-benzyloxy-4-(2-phenethyloxyethoxy)benzene obtained according to the preceding paragraph was dissolved in 200 ml of ethanol and 200 ml of ethyl acetate and hydrogenated overnight at atmospheric pressure and room temperature in the presence of 0.4 g of 10% palladium/carbon. The catalyst was removed by filtration and the filtrate was evaporated to give 10.8 g (91%) of 4-(2-phenethyloxyethoxy)phenol in the form of an oil which was homogeneous according to chromatography.

EXAMPLE 7

Preparation of 1-[2-chloro-4-[2-phenethyloxy)-ethoxy]-phenoxy]-3-isopropylamino-2-propanol hydrochloride In a manner analogous to that described in the first paragraph of Example 6, from 2-chloro-4-(2-phenethyloxyethoxy)-phenol there was obtained 1-[2-chloro-4-[2-(phenethyloxy)ethoxy]phenoxy]-3-isopropylamino-2-propanol hydrochloride of melting point 82°–84° C. (from isopropanol).

The 2-chloro-4-(2-phenethyloxyethoxy)phenol used as the starting material can be prepared as follows:

(a) 8.9 g of 3-chloro-4-benzyloxybenzaldehyde were dissolved in 150 ml of dichloromethane containing 7.3 g of 3-chloroperbenozic acid. The solution was left to stir at room temperature overnight. The mixture was washed with a saturated solution of sodium metabisulfite, followed by a saturated solution of sodium bicarbonate and then water. The organic phase was separated, dried over sodium sulfate, filtered and evaporated to dryness. The residue was dissolved in 100 ml ethanol containing 2.5 g of sodium ethoxide and the solution was stirred at room temperature for 1 hour. The solvent was removed by evaporation and the residue was acidified with 2N hydrochloric acid and subsequently extracted with ethyl acetate. The organic phase was separated, washed with water, dried over sodium sulfate, filtered and evaporated to dryness. The crystalline residue was recrystallized from hexane to give 5.1 g (60%) of 3-chloro-4-benzyloxyphenol of melting point 49°–51° C.

(b) In a manner analogous to that described in Example 6(a), from 4.12 g of 3-chloro-4-benzyloxyphenol there was obtained a crude product which was purified by chromatography on a column of silica gel using chloroform for the elution to give 4.30 g (64%) of 1-benzyloxy-2-chloro-4-(2-phenethyloxyethoxy)-benzene in the form of an oil which was homogeneous according to chromatography.

(c) The 1-benzyloxy-2-chloro-4-(2-phenethyloxyethoxy)-benzene obtained according to the preceding paragraph was stirred in 20 ml of 48% hydrogen bromide in glacial acetic acid at 25° C. for 30 minutes. The solution was evaporated to dryness and the residue was partitioned between 2N aqueous sodium hydroxide and diethyl ether. The aqueous phase was acidified to pH 6 with concentrated hydrochloric acid and extracted with ethyl acetate. The organic extract was washed with water, dried over sodium sulfate, filtered and evaporated to give 2.06 g (76%) of 2-chloro-4-(2-phenethyloxyethoxy)phenol in the form of an oil which was homogeneous according to chromatography.

EXAMPLE 8

Preparation of 1-[2-methyl-4-[2-(phenethyloxy)ethoxy]-phenoxy]-3-isopropylamino-2-propanol hydrochloride In a manner analogous to that described in the first paragraph of Example 6, from 2-methyl-4-(2-phenethyloxy-ethoxy)phenol there was obtained 1-[2-methyl-4-[2-(phenethyloxy)ethoxy]phenoxy]-3-isopropylamino-2-propanol hydrochloride of melting point 85°–87° C. (from ethyl acetate).

The 2-methyl-4-(2-phenethyloxyethoxy)phenol used as the starting material can be prepared as follows:

(a) In a manner analogous to that described in Example 6(a), from 3.0 g of 4-hydroxy-2-methylacetophenone there were obtained 5.90 g (99%) of 2-methyl-4-(2-phenethyloxy-ethoxy)acetophenone in the form of an oil which was homogeneous according to chromatography.

(b) The 2-methyl-4-(2-phenethyloxyethoxy)acetophenone obtained according to the preceding paragraph was dissolved in 80 ml of dichloromethane containing 3.91 g of 3-chloroperbenzoic acid and the solution was left to stand at room temperature for 5 days. The mixture was washed with a saturated solution of sodium metabisulfite, followed by a saturated solution of sodium bicarbonate, dried over sodium sulfate, filtered and evaporated. The crude product was dissolved in 250 ml of methanol containing 2.25 g of sodium methoxide and the mixture was left to stand at room temperature for 1 hour. The solvent was removed by evaporation under reduced pressure and the residue was partitioned between dilute hydrochloric acid and dichloromethane. The organic phase was separated, washed with water, dried over sodium sulfate, filtered and evaporated. The residue was chromatographed on silica gel using 40% chloroform/hexane for the elution. Evaporation of the eluate gave 3.3 g (61%) of 2-methyl-4-(2-phenethyloxy-ethoxy)phenol in the form of an oil which was homogeneous according to chromatography.

EXAMPLE 9

Preparation of 1-[4-[2-(4-methoxyphenethyloxy)-ethoxy]phenoxy]-3-isopropylamino-2-propanol hydrochloride In a manner analogous to that described in the first paragraph of Example 1, from 2.25 g of 1-isopropylamino-3-(4-hydroxyphenoxy)-2-propanol and 2.74 g of 2-[2-(4-methoxyphenyl)ethoxy]ethyl methanesulfonate there were obtained 3.4 g (77%) of 1-[4-[2-(4-methoxyphenethyloxy)-ethoxy]phenoxy]-3-isopropylamino-2-propanol hydrochloride of melting point 99°–101° C. (from isopropanol).

The 2-[2-(4-methoxyphenyl)ethoxy]ethyl methanesulfonate used as the starting material can be prepared as follows:

(a) 6.08 g of 4-methoxyphenethyl alcohol were reacted with 3.8 g of chloroacetic acid in a manner analogous to that described in Example 4(a) to give 6.64 g (79%) of 2-(4-methoxyphenyl)ethoxyacetic acid of melting point 82°–84° C. (from toluene).

(b) The 2-(4-methoxyphenyl)ethoxyacetic acid obtained according to the preceding paragraph was reduced with lithium aluminum hydride in a manner analogous to that described in Example 1(b) to give 5.4 g (96%) of 2-[2-(4-methoxyphenyl)ethoxy]ethanol in the form of an oil which was homogeneous according to chromatography.

(c) The 2-[2-(4-methoxyphenyl)ethoxy]ethanol obtained according to the preceding paragraph was sulfonylated with methanesulfonyl chloride in a manner analogous to that described in Example 1(c) to give 8.05 g (100%) of 2-[2-(4-methoxyphenyl)ethoxy] ethyl methanesulfonate in the form of an oil which was homogeneous according to chromatography.

EXAMPLE 10

Preparation of 1-[4-[2-(4-chlorophenethyloxy)-ethoxy]-phenoxy]-3-isopropylamino-2-propanol hydrochloride In a manner analogous to that described in the first paragraph of Example 1, from 1.08 g of 1-isopropylamino-3-(4-hydroxyphenoxy)-2-propanol and 1.42 g of 2-[2-(4-chlorophenyl)ethoxy]ethyl methanesulfonate there were obtained 1.3 g (57%) of 1-[4-[2-(4-chlorophenethyloxy)-ethoxy]phenoxy]-3-isopropylamino-2-propanol hydrochloride of melting point 99°–101° C. (from ethyl acetate).

The 2-[2-(4-chlorophenyl)ethoxy]ethyl methanesulfonate used as the starting material can be prepared as follows:

(a) 3.15 g of 4-chlorophenethyl alcohol were reacted with 2.2 g of chloroacetic acid in a manner analogous to that described in Example 1(a) to give 4.55 g (91%) of 2-(4-chlorophenyl)ethoxyacetic acid of melting point 75°–77° C. (from ethyl acetate/hexane).

(b) The 2-(4-chlorophenyl)ethoxyacetic acid obtained according to the preceding paragraph was reduced with lithium hydride in a manner analogous to that described in Example 1(b) to give 1.6 g (43%) of 2-[2-(4-chlorophenyl)-ethoxy]ethanol in the form of an oil which was homogeneous according to chromatography.

(c) The 2-[2-(4-chlorophenyl)ethoxy]ethanol obtained according to the preceding paragraph was sulfonylated with methanesulfonyl chloride in a manner analogous to that described in Example 1(c) to give 1.5 g (92%) of 2-[2-(4-chlorophenyl)ethoxy]ethyl methanesulfonate in the form of an oil which was homogeneous according to chromatography.

EXAMPLE 11

Preparation of 1-[2-fluoro-4-[2-(4-fluorophenethyloxy)ethoxy]phenoxy]-3-isopropylaminopropanol p-toluenesulfonate In a manner analogous to that described in the first paragraph of Example 6, from 2-fluoro-4-[2-(4-fluorophenethyloxy)ethoxy]phenol there was obtained 1-[2-fluoro-4-[2-4-fluorophenethyloxy)ethoxy]phenoxy]-3-isopropylamino-2-propanol p-toluenesulfonate of melting point 77°–80° C. (from isopropanol).

The 2-fluoro-4-[2-(4-fluorophenethyloxy)ethoxy]-phenol used as the starting material can be prepared as follows:

(a) 4.32 g of 3-fluoro-4-hydroxyacetophenone in 50 ml of dimethylformamide were treated with 1.35 g of a 50% sodium hydride dispersion in mineral oil and the mixture was stirred for 5 minutes. 4.79 g of benzyl bromide were added and the mixture was heated at 60° C. for 0.5 hour with stirring. The mixture was evaporated to dryness and the residue was partitioned between 1N sodium hydroxide solution and ethyl acetate. The organic phase was separated, washed well with water, dried over sodium sulfate, filtered and evaporated. Recrystallization of the yellow solid residue from ethyl acetate/petrol gave 4.99 g (73%) of 3-fluoro-4-benzyloxyacetophenone of melting point 82°–85° C.

(b) The substituted-acetophenone obtained according to the preceding paragraph was dissolved in 100 ml of dichloromethane containing 4.12 g of 3-chloroperbenzoic acid and the solution was left to stand at room temperature for 5 days. The mixture was washed with a saturated solution of sodium metabisulfite and then with a saturated solution of sodium bicarbonate, dried over sodium sulfate, filtered and evaporated. The crude product was dissolved in 100 ml of methanol containing 1.2 g of sodium methoxide and the mixture was left to stand at room temperature for 5 minutes. The solvent was removed by evaporation under reduced pressure and the residue was partitioned between dilute hydrochloric acid and ethyl acetate. The organic phase was separated, washed with water, dried over sodium sulfate, filtered and evaporated. The residue was crystallized from methylcyclohexane to give 2.53 g (57%) of 3-fluoro-4-benzyloxyphenol of melting point 80°–82° C.

(c) In a manner analogous to that described in Example 6(a), from 2.42 g of 3-fluoro-4-benzyloxyphenol and 2.91 g of 2-[2-(4-fluorophenyl)ethoxy]ethyl methanesulfonate [prepared as described in Example 2(a)] there were obtained 4.23 g (99%) of 1-benzyloxy-2-fluoro-4-[2-(4-fluorophenethyloxy)ethoxy]benzene in the form of an oil which was homogeneous according to chromatography.

(d) In a manner analogous to that described in Example 6(b), the foregoing 1-benzyloxy-2-fluoro-4-[2(4-fluorophenethyloxy)ethoxy]benzene was debenzylated to give 2.95 g (91%) of 2-fluoro-4-[2-(4-fluorophenethyloxy)ethoxy]phenol in the form of an oil which was homogeneous according to chromatography.

EXAMPLE 12

Preparation of 1-[3-fluoro-4-[2-(4-fluorophenethyloxy)ethoxy]phenoxy]-3-isopropylamino-2-propanol hydrochloride In a manner analogous to that described in the first paragraph of Example 6, from 3-fluoro-4-[2-(4-fluorophenethyloxy)ethoxy]phenol there was obtained 1-[3-fluoro-4-[2-(4-fluorophenethyloxy)ethoxy]phenoxy]-3-isopropylamino-2-propanol hydrochloride of melting point 74°–76° C. (from isopropanol).

The 3-fluoro-4-[2-(4-fluorophenethyloxy)ethoxy]phenol used as the starting material can be prepared as follows:

(a) In a manner analogous to that described in Example 6(a), from 1.21 g of 3-fluoro-4-hydroxyacetophenone and 2.06 g of 2-[2-(4-fluorophenyl)ethoxy]ethyl methanesulfonate [prepared as described in Example 2(a)] there were obtained 2.18 g (87%) of 3-fluoro-4-[2-(4-fluorophenethyloxy)ethoxy]acetophenone in the form of an oil which was homogeneous to chromatography.

(b) The substituted-acetophenone obtained according to the preceding paragraph was dissolved in 30 ml of dichloromethane containing 1.38 g of 3-chloroperbenzoic acid and the solution was left to stand at room temperature for 5 days. The mixture was washed with a saturated solution of sodium metabisulfite and then with a saturated solution of sodium bicarbonate, dried over sodium sulfate, filtered and evaporated. The crude product was dissolved in 50 ml of methanol containing 0.4 g of sodium methoxide and the mixture was left to stand at room temperature for 1 hour. The solvent was removed by evaporation under reduced pressure and the residue was partitioned between dilute hydrochloric acid and dichloromethane. The organic phase was separated, washed with water, dried over sodium sulfate, filtered and evaporated. The residue was chromatographed over silica gel using 70% chloroform/hexane for the elution. Evaporation of the eluate gave 1.0 g (50%) of 3-fluoro-4-[2-(4-fluorophenethyloxy)ethoxy]phenol in the form of an oil which was homogeneous according to chromatography.

EXAMPLE 13

Preparation of 1-[4-[2-(2,4-difluorophenethyloxy)ethoxy]phenoxy]-3-isopropylamino-2-propanol hydrochloride In a manner analogous to that described in the first paragraph of Example 1, from 2.52 g of 1-isopropylamino-3-(4-hydroxyphenoxy)-2-propanol and 3.12 g of 2-[2-(2,4-difluorophenyl)ethoxy]ethyl methanesulfonate there were obtained 2.3 g (46%) of 1-[4-[2-(2,4-difluorophenethyloxy)-ethoxy]phenoxy]-isopropylamino-2-propanol hydrochloride of melting point 69°–72° C. (from isopropanol/diethyl ether).

The 2-[2-(2,4-difluorophenyl)ethoxy]ethyl methanesulfonate used as the starting material can be prepared as follows:

(a) 25.7 g of 2,4-difluorobenzyl bromide dissolved in 100 ml of tetrahydrofuran were added dropwise to a stirred suspension of 3.0 g of magnesium turnings in 30 ml of tetrahydrofuran over a period of 0.5 hour. The mixture was stirred for an additional 10 minutes after completion of the addition and then a steady stream of carbon dioxide was bubbled through the Grignard reagent for 1 hour. The mixture was evapoerated to dryness and the residue was partitioned between diethyl ether and the dilute hydrochloric acid. The diethyl ether phase was separated and extracted with 2N sodium hydroxide solution. The alkaline extract was acidified with concentrated hydrochloric acid and the product was extracted with diethyl ether to give 5.1 g (24%) of crude 2,4-difluorophenylacetic acid which, without purification, was dissolved in 25 ml of tetrahydrofuran and added dropwise to a stirred suspension of 2.0 g of lithium aluminum hydride in 100 ml of tetrahydrofuran. After completion of the addition, stirring was continued for 1 hour. Excess lithium aluminum hydride was destroyed by the dropwise addition of 2 ml of water in 20 ml of tetrahydrofuran followed by 2 ml of 15% sodium hydroxide and then 6 ml of water. The suspension was filtered through a filter-aid, which was washed well with diethylether, and the combined filtrate and washings were evaporated to dryness. The residue was dissolved in dichloromethane, dried over sodium sulfate, filtered and evaporated to give 3.95 g (84%) of 2,4-difluorophenethyl alcohol in the form of an oil which was homogeneous according to chromatography.

(b) 3.63 g of 2,4-difluorophenethyl alcohol were reacted with 2.17 g of chloroacetic acid in a manner analogous to that described in Example 1(a), except that the reaction mixture was heated at 120° C. for 1 hour, to give 2.7 g (54%) of 2-(2,4-difluorophenyl)ethoxyacetic acid in the form of an oil which was homogeneous according to chromatography.

(c) The 2-(2,4-difluorophenyl)ethoxyacetic acid obtained according to the preceding paragraph was reduced with lithium aluminum hydride in a manner analogous to that described in Example 1(b) to give 2.31 g (93%) of 2-[2-(2,4-dufluorophenyl)ethoxy]ethanol in the form of an oil which was homogeneous according to chromatography.

(d) The 2-[2-(2,4-difluorophenyl)ethoxy]ethanol obtained according to the preceding paragraph was dissolved in 40 ml of dichloromethane containing 1.13 g of triethylamine and the solution was treated with 1.28 g of methanesulfonyl chloride. After stirring for 15 minutes, the solution was washed well with water, the organic layer was separated, dried over sodium sulfate, filtered and evaporated to give 3.12 g (100%) of 2-[2-(2,4-difluorophenyl)ethoxy]ethyl methanesulfonate in the form of an oil which was homogeneous according to chromatography.

The following Examples illustrate typical pharmaceutical preparations containing the substituted phenoxyaminopropanol derivatives provided by the present invention:

EXAMPLE A

Tablets containing the following ingredients can be produced in a conventional manner:

| Ingredient | Per tablet |
|---|---|
| A substituted phenoxy-aminopropanol derivative of the invention | 25 mg |
| Lactose | 103 mg |
| Starch | 61 mg |
| Magnesium stearate | 11 mg |
| Total weight | 200 mg |

EXAMPLE B

A capsule formulation containing the following ingredients can be produced in a conventional manner:

| Ingredient | Per capsule |
|---|---|
| A substituted phenoxy-aminopropanol derivative of the invention | 25 mg |
| Lactose | 106 mg |
| Starch | 20 mg |
| Talc | 9 mg |
| Total weight | 160 mg |

What is claimed is:

1. A compound of the formula

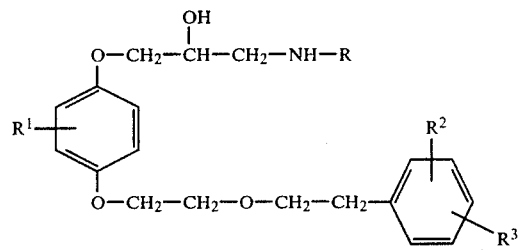

wherein R is a branched-chain alkyl of 3 or 4 carbons, $R^1$ is hydrogen or fluorine and $R^2$ is fluorine and $R^3$ is hydrogen or fluorine, or a pharmaceutically acceptable acid addition salt thereof.

2. A compound in accordance with claim 1, wherein $R^1$ is in the ortho-position to the 3-alkylamino-2-hydroxypropoxy group and $R^3$ is hydrogen, or a pharmaceutically acceptable acid addition salt thereof.

3. A compound in accordance with claim 1 or claim 2, wherein R is isopropyl or tert.butyl, or a pharmaceutically acceptable acid addition salt thereof.

4. A compound in accordance with claim 1, 1-[4-[2-(4-fluorophenethyloxy)ethoxy]phenoxy]-3-isopropylamino-2-propanol or a pharmaceutically acceptable acid addition salt thereof.

5. A pharmaceutical composition comprising a compound of the formula

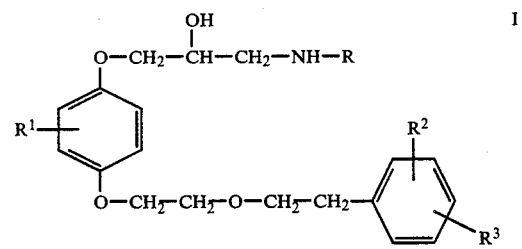

wherein R is a branched-chain alkyl of 3 or 4 carbon atoms, $R^1$ is hydrogen or fluorine and $R^2$ is fluorine and $R^3$ is hydrogen or fluorine, or a pharmaceutically acceptable acid addition salt thereof, and a pharmaceutically inert carrier material.

6. A pharmaceutical composition in accordance with claim 5, wherein the compound of formula I is 1-[4-[2-(4-fluorophenethyloxy)ethoxy]phenoxy]-3-isopropylamino-2-propanol or a pharmaceutically acceptable acid addition salt thereof.

7. A cardioselective β-adrenergic blocking composition comprising a compound of the formula 1-[4-[2-(4-fluorophenethyloxy)ethoxy]phenoxy]-3-isopropylamino-2-propanol or a pharmaceutically acceptable acid addition salt thereof, and a pharmaceutically inert carrier material.

8. An antihypertensive composition comprising a compound of the formula 1-[4-[2-(4-fuorophenethyloxy)ethoxy]phenoxy]-3-isopropylamino-2-propanol or a pharmaceutically acceptable acid addition salt thereof, and pharmaceutically inert carrier material.

9. A method of treating angina pectoris which comprises administering an effective amount of a compound of the formula

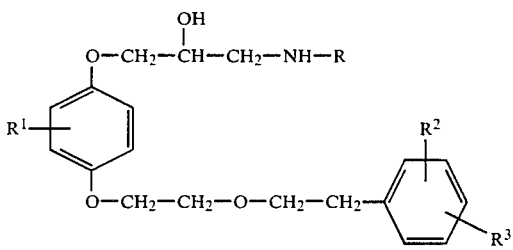

wherein R is a branched-chain alkyl of 3 or 4 carbon atoms, $R^1$ is hydrogen or fluorine and $R^2$ is fluorine and $R^3$ is hydrogen or fluorine, or a pharmaceutically acceptable salt thereof.

10. A method in accordance with claim 9 wherein the compound of formula I is 1-[4-[2-(4-fluorophenethyloxy)ethoxy]phenoxy]-3-isopropylamino-2-propanol or a pharmaceutically acceptable acid addition salt thereof.

11. A method of treating cardiac arrhythmias which comprises administering an effective amount of a compound of the formula

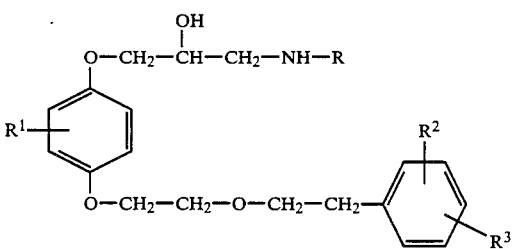

wherein R is a branched-chain alkyl of 3 or 4 carbon atoms, $R^1$ is hydrogen or fluorine and $R^2$ is fluorine and $R^3$ is hydrogen or fluorine, or a pharmaceutically acceptable acid addition salt thereof.

12. A method in accordance with claim 11 wherein the compound of formula I is 1-[4-[2-(4-fluorophenethyloxy)ethoxy]phenoxy]-3-isopropylamino-2-propanol or a pharmaceutically acceptable acid addition salt thereof.

13. A method of treating hypertension which comprises administering an effective amount of a compound of the formula

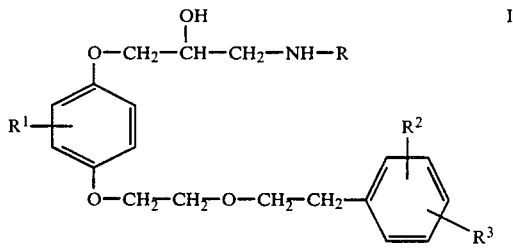

wherein R is a branched-chain alkyl of 3 or 4 carbon atoms, $R^1$ is hydrogen or fluorine and $R^2$ is fluorine and $R^3$ is hydrogen or fluorine, or a pharmaceutically acceptable acid addition salt thereof.

14. A method in accordance with claim 13 wherein the cmpound of formula I is 1-[4-[2-(4-fluorophenethyloxy)ethoxy]phenoxy]-3-isopropylamino-2-propanol or a pharmaceutically acceptable acid addition salt thereof.

15. A compound, in accordance with claim 1, selected from the group consisting of 1-[2-fluoro-4-[2-(4-fluorophenethyloxy)ethoxy]phenoxy]-3-isopropylamino-2-propanol, 1-[3-fluoro-4-[2-(4-fluorophenthyloxy)ethoxy]phenoxy]-3-isopropylamino-2-propanol, 1-[4-[2-(2,4-difluorophenethyloxy)ethoxy]phenoxy]-3-isopropylamino-2-propanol or a pharmaceutically acceptable acid addition salt thereof.

* * * * *

UNITED STATES PATENT AND TRADEMARK OFFICE
CERTIFICATE OF CORRECTION

PATENT NO. : 4,649,160
DATED : March 10, 1987
INVENTOR(S) : Peter James Machin

It is certified that error appears in the above—identified patent and that said Letters Patent is hereby corrected as shown below:

On the title page, on the first line under the heading Foreign Application Priority Data "May 2, 1980   GB   United Kingdom ..... 8017583"

should be

June 2, 1980   GB   United Kingdom ..... 8017983

Signed and Sealed this

First Day of December, 1987

Attest:

DONALD J. QUIGG

Attesting Officer

Commissioner of Patents and Trademarks